United States Patent [19]

Adams et al.

[11] Patent Number: 5,531,764

[45] Date of Patent: Jul. 2, 1996

[54] IMPLANTABLE DEFIBRILLATOR SYSTEM AND METHOD HAVING SUCCESSIVE CHANGEABLE DEFIBRILLATION WAVEFORMS

[75] Inventors: Theodore P. Adams, Edina; Mark W. Kroll, Minnetonka, both of Minn.

[73] Assignee: Angeion Corporation, Plymouth, Minn.

[21] Appl. No.: 227,563

[22] Filed: Apr. 14, 1994

Related U.S. Application Data

[63] Continuation of Ser. No. 856,982, Mar. 24, 1992, abandoned.

[51] Int. Cl.⁶ .................................................. A61N 1/39
[52] U.S. Cl. ...................................... 607/5; 607/15
[58] Field of Search .............................. 607/5, 4, 6, 7, 607/8, 13

[56] References Cited

U.S. PATENT DOCUMENTS

| | | | |
|---|---|---|---|
| 4,708,145 | 11/1987 | Tacker, Jr. et al. | 128/419 D |
| 4,727,877 | 3/1988 | Kallok | 128/419 D |
| 4,800,883 | 1/1989 | Winstrom . | |
| 4,830,006 | 5/1989 | Haluska . | |
| 4,850,357 | 7/1989 | Bach, Jr. . | |
| 4,953,551 | 9/1990 | Mehra et al. | 128/419 D |
| 5,107,834 | 4/1992 | Ideker et al. | 128/419 D |
| 5,133,353 | 7/1992 | Hauser . | |
| 5,163,427 | 11/1992 | Keimel . | |
| 5,184,616 | 2/1993 | Weiss . | |
| 5,199,429 | 4/1993 | Kroll . | |
| 5,385,574 | 1/1995 | Hauser et al. . | |

FOREIGN PATENT DOCUMENTS

| | | | |
|---|---|---|---|
| 0280526 | 2/1988 | European Pat. Off. . | |
| 0280526 | 8/1988 | European Pat. Off. | 128/419 D |

OTHER PUBLICATIONS

Medtronic^R PCT^TM Device Tachyarrhythima Control System Reference Guide Apr. 1992.
Ventritex^R Cadence^R Tiered Therapy Defibrillator System Cadence Model V–100 and Cadence Programmer, Prel. Physician's Manual, Oct. 1990.
Ventak^R PRx^TM 1700/1705 Physician's Manual, Cardiac Pacemarks, Inc.

*Primary Examiner*—William E. Kamm
*Assistant Examiner*—Scott M. Getzow
*Attorney, Agent, or Firm*—Patterson & Keough

[57] ABSTRACT

An implantable defibrillator having programmable shock waveforms and paths where each successive waveform may be of a different shape and form, and delivered to and through an area of the human heart in a desired sequence. The shock waveforms can be delivered independently through certain areas of the heart or through different areas of the heart to the can electrode or to a patch electrode at a computed common time. Alternatively, a first shock waveform or set of shock waveforms can be delivered through one or more areas of the heart followed by a delivery of time sequenced delayed shock waveform or forms through specific areas of the heart to the can electrode or patch electrode.

6 Claims, 15 Drawing Sheets

IMPLANTABLE DEFIBRILLATOR SYSTEM AND METHOD HAVING SUCCESSIVE CHANGEABLE DEFIBRILLATION WAVEFORMS

CROSS REFERENCES TO CO-PENDING APPLICATIONS

This is a Continuation of Ser. No. 08/856,982, now abandoned, filed Mar. 24, 1992.

BACKGROUND OF THE INVENTION

1. Field of the Invention

The present invention pertains to the field of heart defibrillators, and more particularly, relates to delivery of programmable and sequenced waveforms to areas of the heart by the components of a defibrillator.

2. Description of the Prior Art

Prior art defibrillators deliver a number of successive shocks for heart defibrillation. The same waveform in these devices is repeated in succession usually to deliver four shock waveforms. The particular handicap or drawback with these devices is that the repeated similar waveforms are determined by the manufacturer, and cannot be changed unless a reimplant of the device is accomplished. The prior art devices used only a repeated similar waveform instead of waveforms of different magnitudes and shapes to accomplish the defibrillation process.

The present invention overcomes the inadequacies of the prior art by providing a programmable defibrillator which can deliver shock waveforms of different shapes and magnitude in different combinations of sequences which are field programmable by a physician.

SUMMARY OF THE INVENTION

Once an implantable defibrillator has determined that the heart is in fibrillation, it begins a sequence of activities that involve charging the output capacitors and verifying that fibrillation is still present before delivering the first shock pulse. After a shock pulse is delivered, the device continues to monitor the heart rate, and if it determines that the shock was unsuccessful in terminating the fibrillation, the implanted defibrillator will deliver a second shock, at the same or higher energy. This sequence can be repeated several times up to four times in currently available devices, after which the device terminates further attempts at conversion. The rationale for terminating therapy after four shocks is that further attempts are unlikely to be successful in that conversion thresholds tend to increase with time in a fibrillation episode, and after fibrillating for long periods, the patient is likely to have suffered irreversible brain damage. In addition, if the shocks are being delivered inappropriately due to noise on the leads or component failure, the patient will receive no more than four unnecessary shocks. The device resets itself after the heart rate has slowed to a normal level for a prescribed length of time.

There is considerable evidence in the literature that some shock waveforms have generally lower defibrillation thresholds than others. However, there are many exceptions to the general rule and for any given patient and/or for different electrode configurations, the most efficient shock waveform may not be the one installed in the implanted prior art device.

The general purpose of this implantable defibrillator is that the shock waveform is programmable so that the implanting physician can select the waveform that yields the lowest threshold for a given patient and electrode configuration.

Further, the invented implantable defibrillator allows the physician to program the device such that each successive shock waveform may be programmed independently. The rationale is that if the first and earliest shock failed, it would be better to try a new waveform on the next shock rather than to repeat a shock waveform that has just demonstrated failure to defibrillate.

According to one embodiment of the present invention, there is provided an implantable defibrillator including a patch electrode for application to the heart, and another lead having sensing electrodes and defibrillation electrodes which are aligned in the right atrium and the right ventricle. A physician-programmable computer, including a memory for storing programmable waveform information, is included in the can of the defibrillator.

One significant aspect and feature of the present invention is a defibrillator which is physician programmable.

Another significant aspect and feature of the present invention is a defibrillator which has a variety of waveforms which can be sequentially applied in the defibrillation process.

A further significant aspect and feature of the present invention is the selective steering of desired waveforms through the heart to the components of the defibrillator.

Still another significant aspect and feature of the present invention is time-sequenced delays of waveform application.

Having thus described one embodiment of the present invention, it is the principal object hereof to provide a programmable defibrillation for the delivery of sequenced, independently shaped and time-sequenced defibrillation shock waveforms to the human heart.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
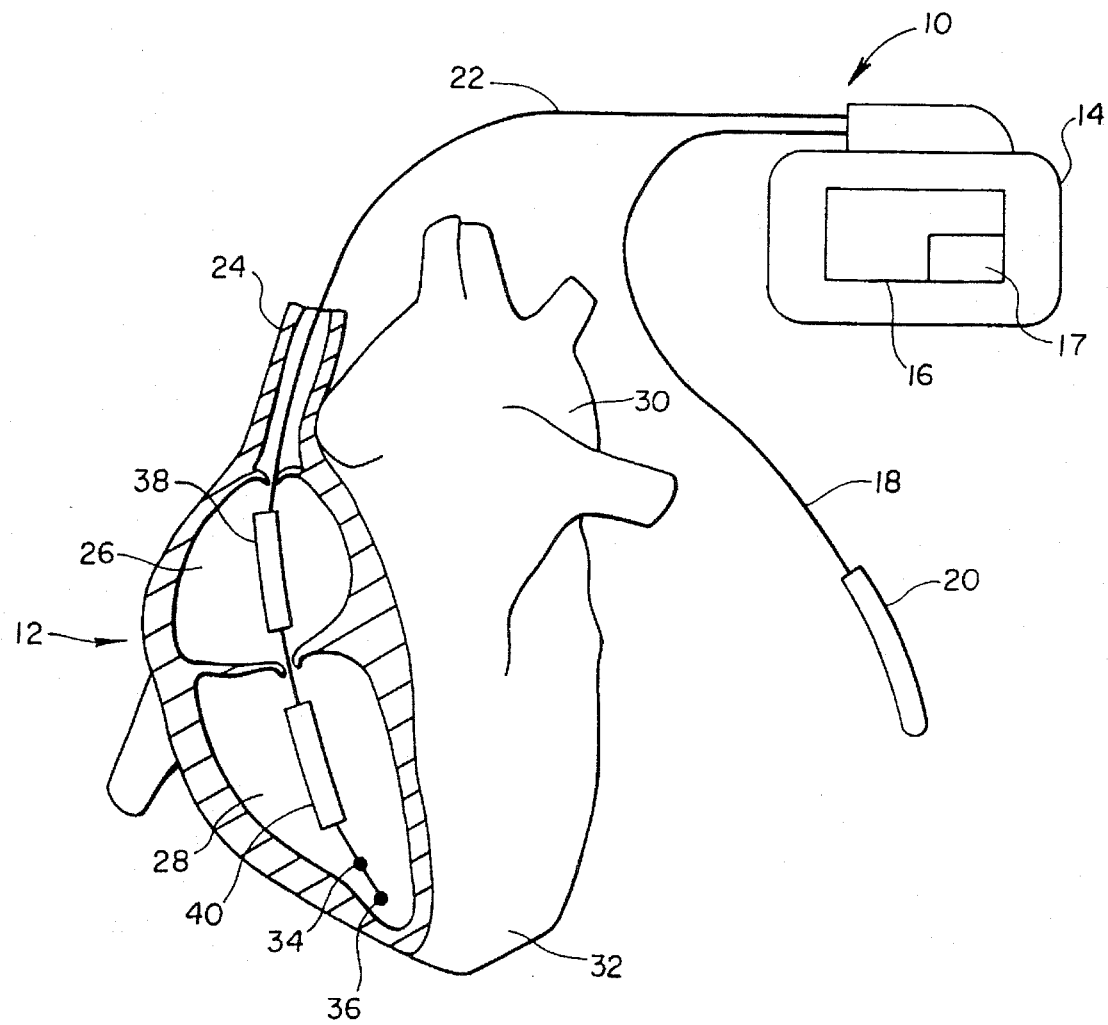
FIG. 1 illustrates an implantable programmable defibrillator, the present invention, connected to a heart.

FIG. 1 illustrates an implantable defibrillator 10 and associated components connected to a heart 12. The implantable defibrillator 10 includes a can 14, which is an electrode, a physician-programmable computer 16, including a memory 17 for storing programmable waveform information, a lead 18 connecting a patch electrode 20 to the implantable defibrillator 10, and a lead 22 having second electrodes connecting to the heart 12. Lead 22 extends through the superior vena cava 24, the right atrium 26, and to the lower region of the right ventricle 28. Also illustrated are the left atrium 30 and the left ventricle 32. Sense electrodes 34 and 36 are located at the distal end of the lead 22, and align in the lower region of the right atrium 26. The lead 22 also includes shock electrodes 38 and 40. The shock electrode 38 aligns in the upper portion of the right atrium 26 and a portion of the superior vena cava 24. Shock electrode 40 aligns centrally in the right ventricle 28.

FIGS. 2, 3, 4, and 5 illustrate representative waveforms that can be formed by the physician-programmable computer 16 of FIG. 1. The formation of these waveforms is the subject matter of a patent entitled IMPLANTABLE DEFIBRILLATOR SYSTEM EMPLOYING CAPACITOR SWITCHING NETWORK, Ser. No. 07/704,619, filed May 23, 1991, now issued as U.S. Pat. No. 5,199,429 having the same assignee. Although FIGS. 2, 3, 4 and 5 illustrate useful waveforms, it is appreciated that any other waveforms can also be incorporated within the teachings of the present invention.

Figure 2:
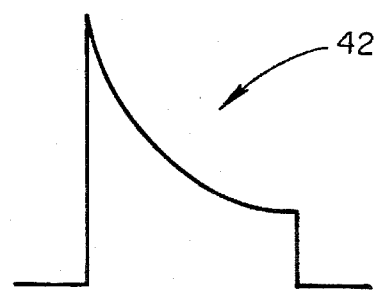
FIG. 2 illustrates a representative waveform.

FIG. 2 illustrates a truncated shock waveform 42 formed by two capacitors in series.

Figure 3:
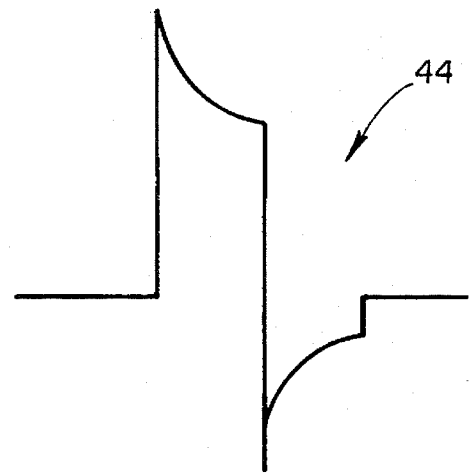
FIG. 3 illustrates another representative waveform.

FIG. 3 illustrates a truncated shock waveform 44 formed by two capacitors in series and having the polarity reversed.

Figure 4:
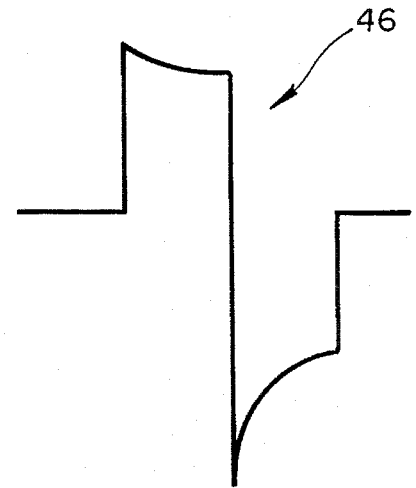
FIG. 4 illustrates another representative waveform.

FIG. 4 illustrates a truncated shock waveform 46 formed by two capacitors in parallel, and have the polarity reversed and series connected.

Figure 5:
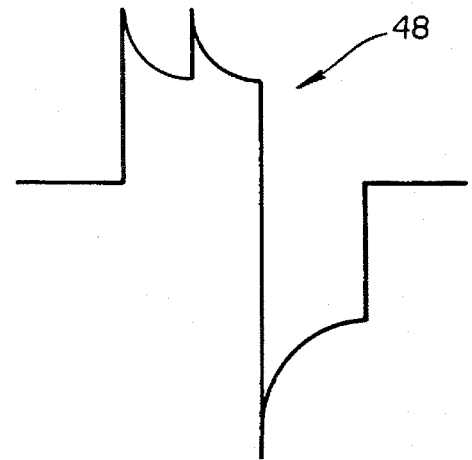
FIG. 5 illustrates another representative waveform.

FIG. 5 illustrates a truncated shock waveform 48 formed by two capacitors sequential, truncated, polarity reversed, and series connected.

MODE OF OPERATION

The waveforms 42–48 illustrated in FIGS. 2–5 can be programmed to be delivered as shock waves in almost any number of sequential arrangements such as four identical sequential shock waveforms such as four successive applications of truncated shock waveform 42, or four sequential truncated shock waveform 44 and following in the same sequential pattern application for identical truncated shock waveforms 46 and 48.

In the alternative, any combination of shock waveforms, such as sequence incorporating a sequence of shock waveforms such as 42, 44, 46, 48. Even a shock waveform sequence where certain shock waveforms are repeated such as 42, 46, 46, 48 can be used. Any desirable sequence can be used whether only one type of waveform is sequentially repeated or whether two or more waveforms are repeated. Any combination or permutation of the sequences may be used as desired.

Figure 6:
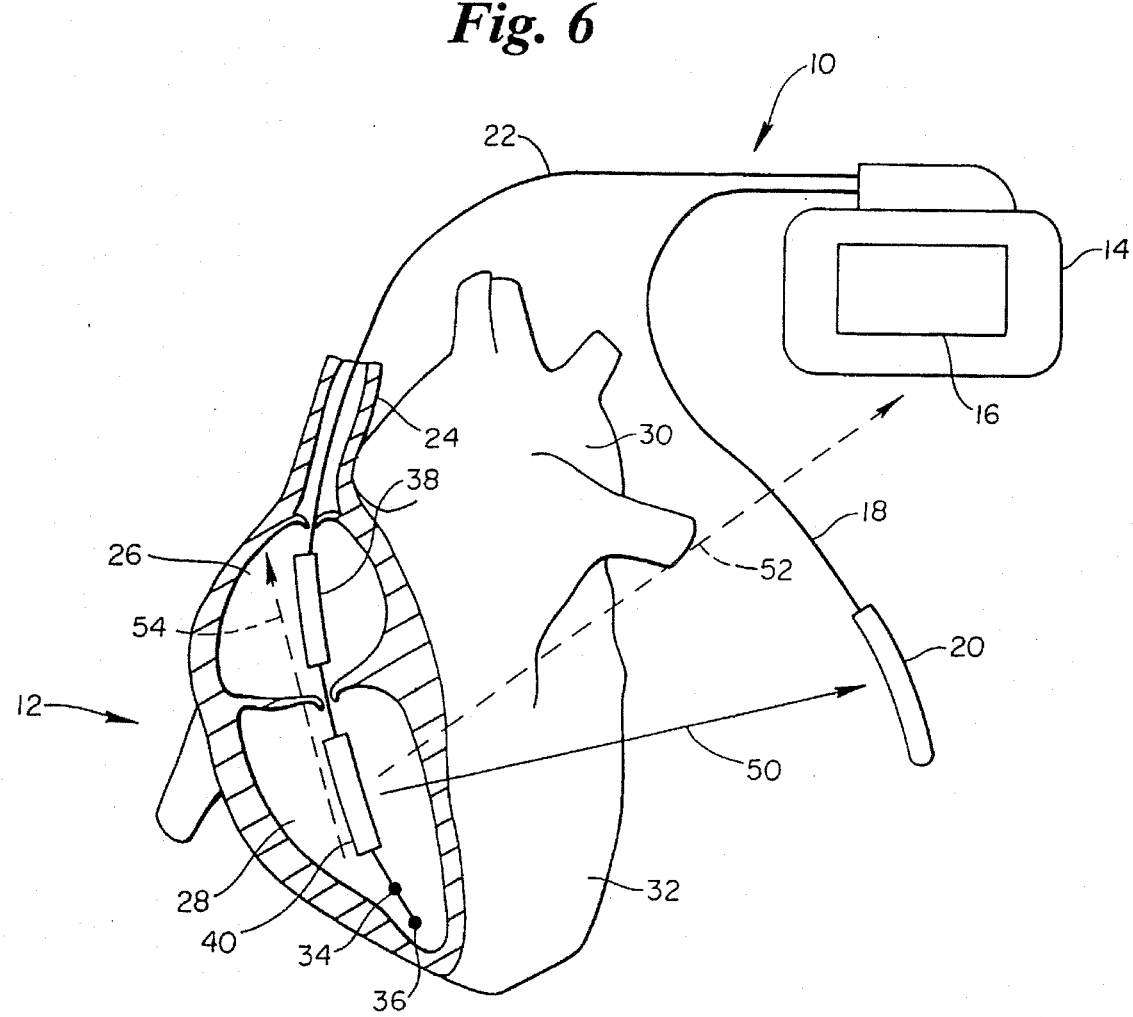
FIG. 6 illustrates shock waveform paths from the heart to the implantable programmable defibrillator.
Figure 7:
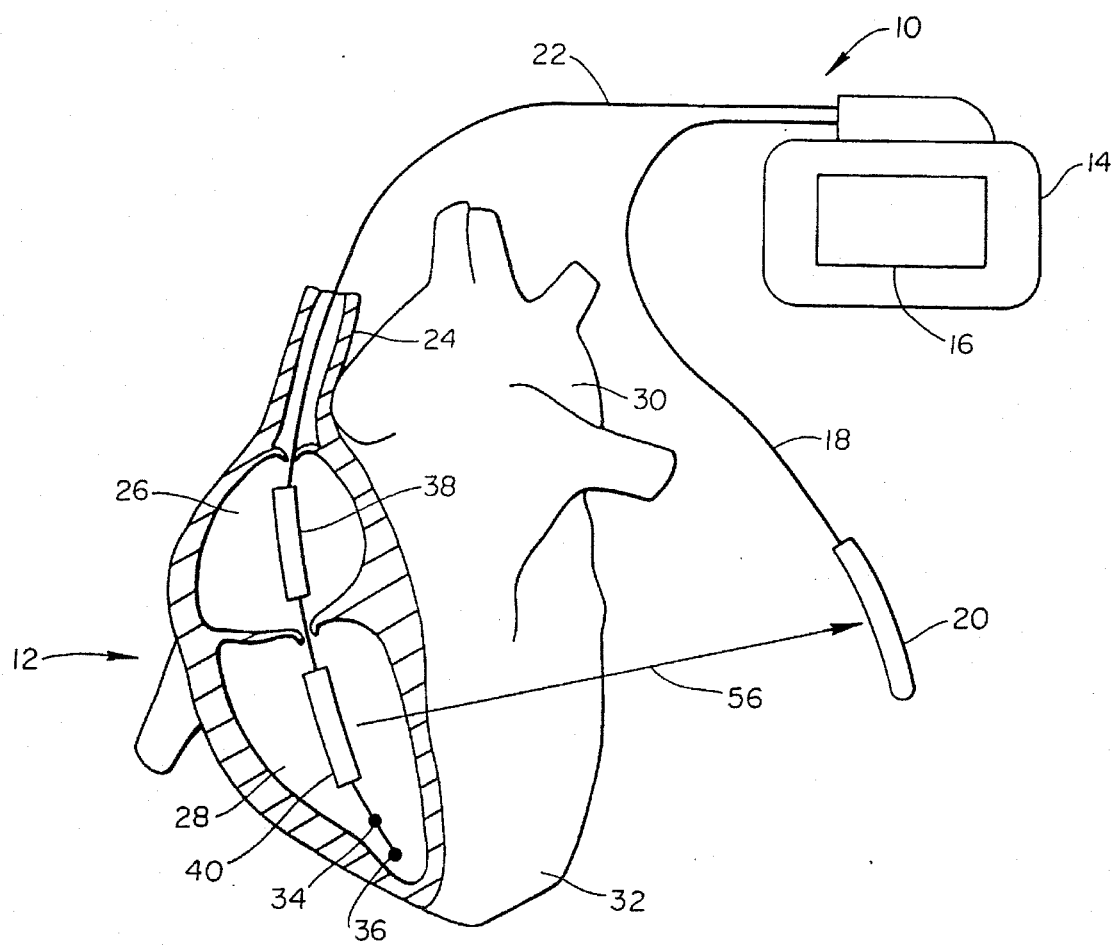
FIG. 7 illustrates another set of waveform paths from the heart to the implantable programmable defibrillator.
Figure 8:
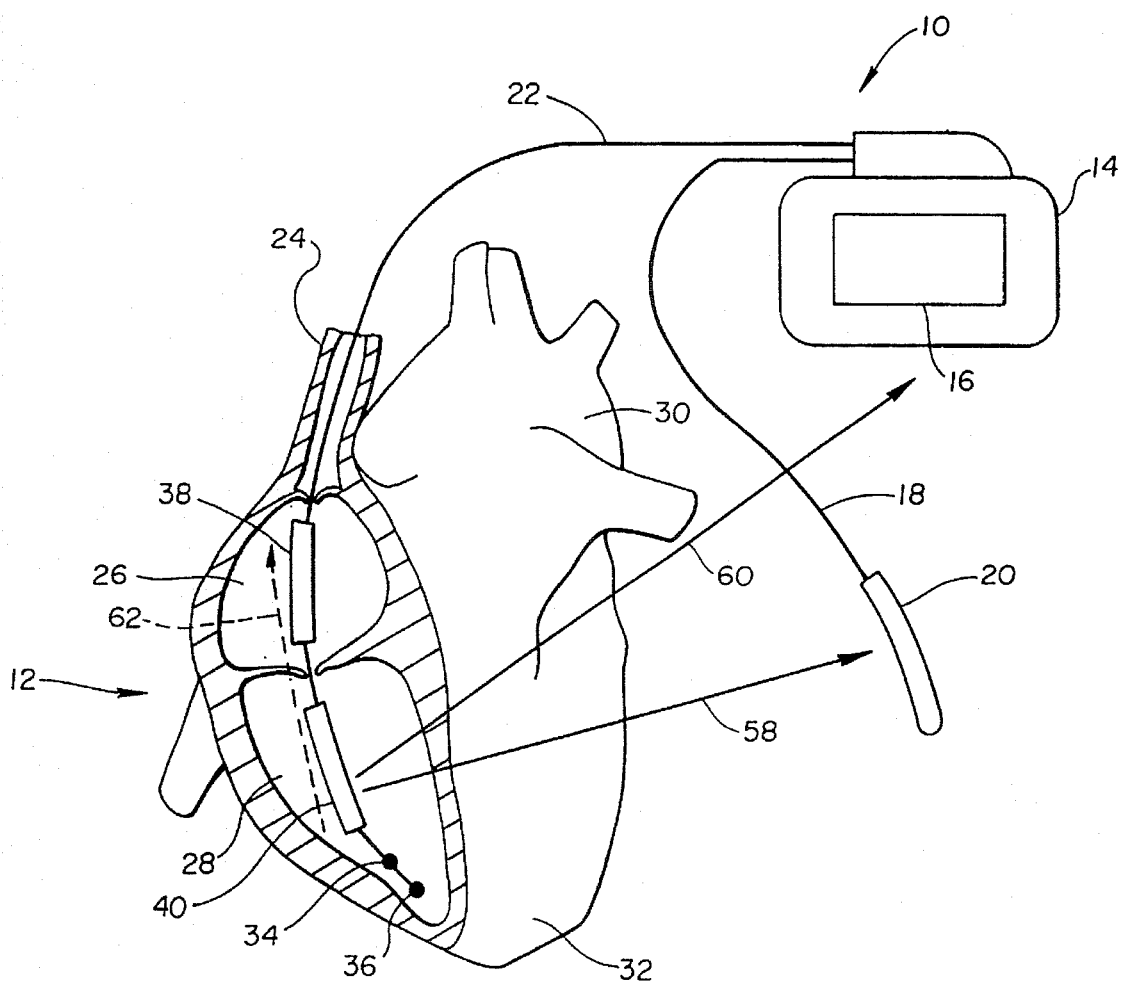
FIG. 8 illustrates another set of waveform paths from the heart to the implantable programmable defibrillator.

FIGS. 6–8 illustrate the principle of successive changeable pathways for detected and programmed delivery of simultaneous or delayed shock sequenced delivery to and about various areas of the heart. The physician-programmable computer 16 detects fibrillation, and from that criteria decides within programmed limits and parameters as set by a physician where and when to deliver defibrillation shocks. All numerals in FIGS. 6–19 correspond to those elements previously described. Shock waveforms sent directly to, from or through a heart area to a defibrillator component are indicated by a path arrow having a solid shaft, such as arrow 50 in FIG. 6. Shock waveforms which are delayed are represented by a path arrow having a dashed shaft such as arrow 52 in FIG. 6. The shock waveforms which are sent are those shock waves such as described in FIGS. 2, 3, 4 and 5. Again, any of the shock waveforms such as waveforms 42–48 can be incorporated and sent directly or delayed across any of the paths whether the path is a directly-sent path or a time-delay path. The shock waves emanate from the shock electrode 40 in the right ventricle 28 in FIGS. 6–19, and travel through ports of the heart to either shock electrode 38, can electrode 14, or patch electrode 20.

FIG. 6 illustrates directly sent shock waveform path 50 traveling through the right ventricle 28 to the patch electrode 20, and delayed shock waveform paths 52 and 54 traveling from the right ventricle 28 to the can electrode 14 and to the shock electrode 38 in the superior vena cava 24.

FIG. 7 illustrates a directly sent shock waveform path 56 traveling through right ventricle 28 to the patch electrode 20 where the can electrode 14 is off.

FIG. 8 illustrates directly sent shock waveform paths 58 and 60 traveling, respectively, through the right ventricle 28, to the patch electrode 20 and the can electrode 14, and a delayed shock waveform path 62 traveling from the right ventricle 28, to the electrode 38 in the superior vena cava 24.

Figure 9:
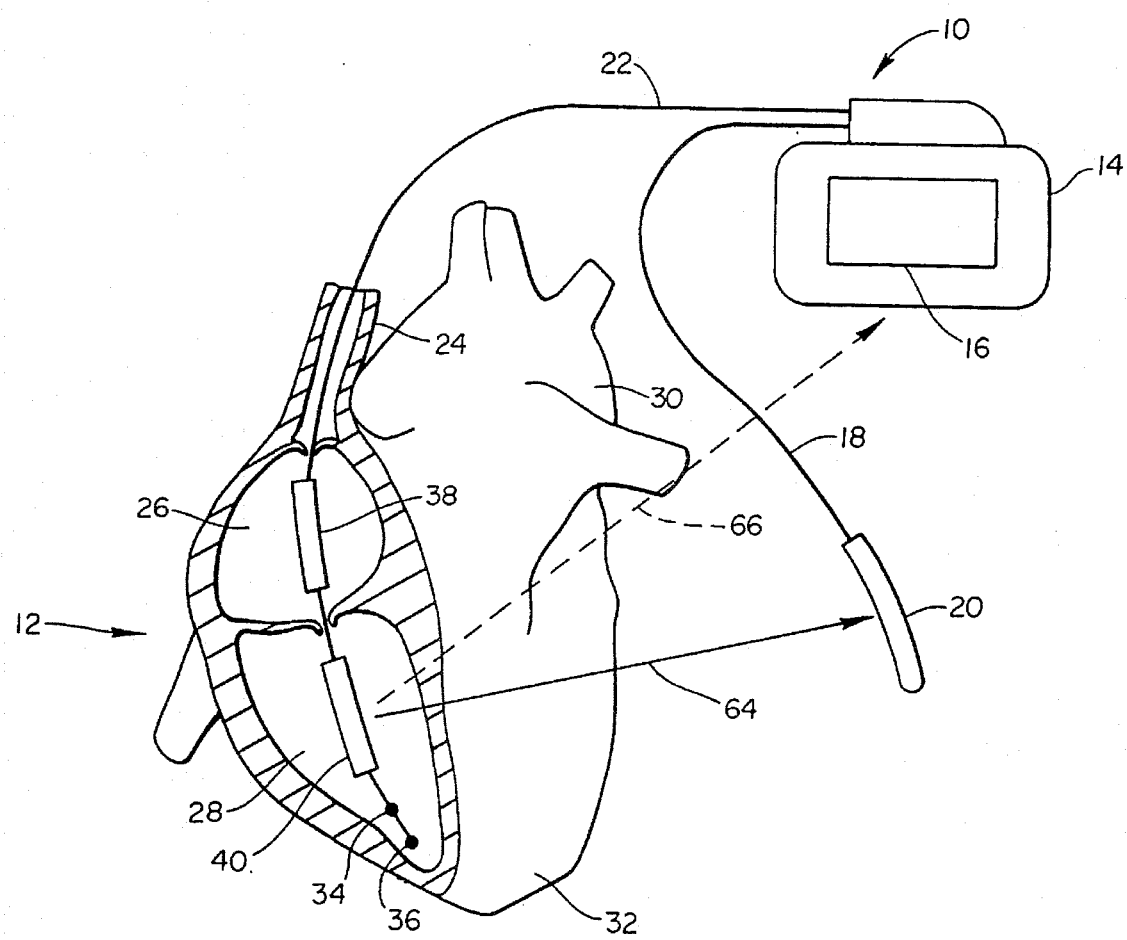
FIG. 9 illustrates another set of waveform paths from the heart to the implantable programmable defibrillator.

FIG. 9 illustrates a directly sent waveform path 64 traveling through the right ventricle 28, to the patch electrode 20, and a delayed shock waveform path 66 traveling from the right ventricle 28, to the can electrode 14. The shock electrode 38 is not connected.

Figure 10:
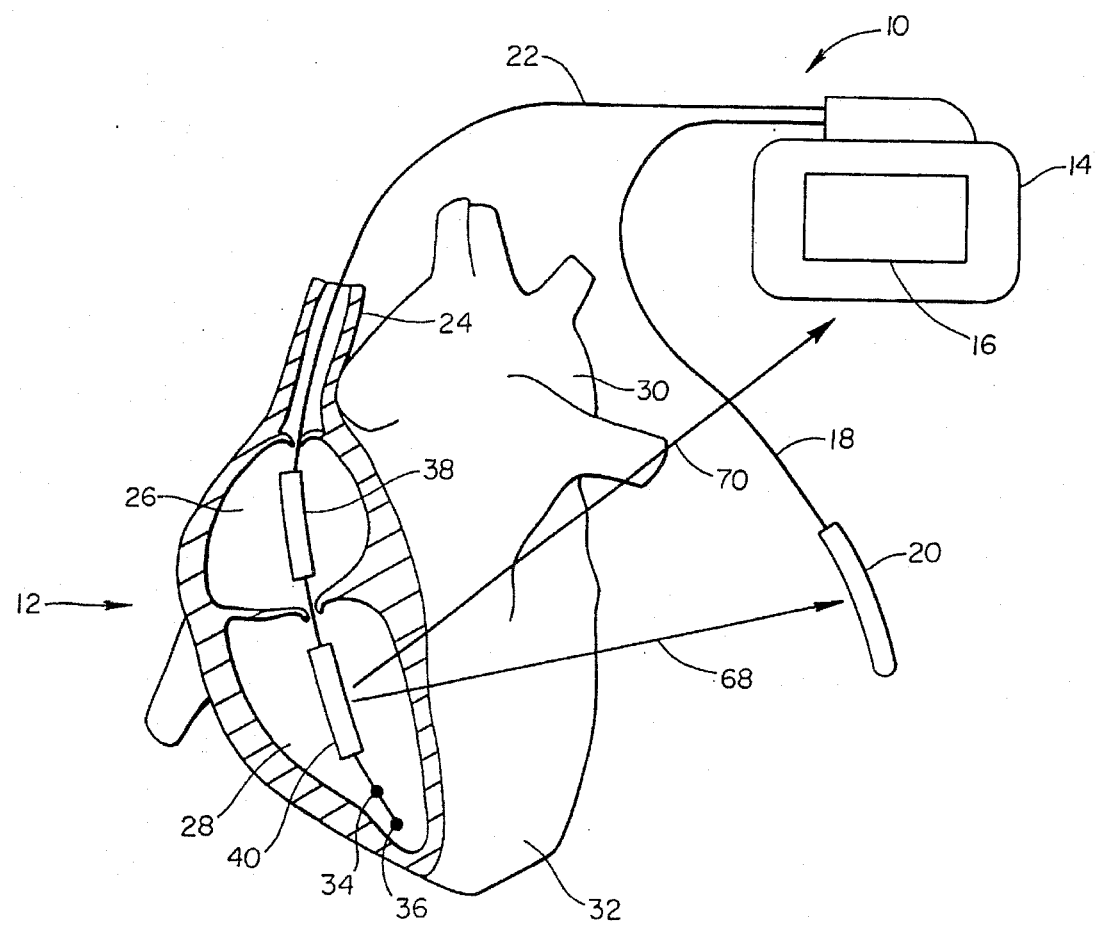
FIG. 10 illustrates another set of waveform paths from the heart to the implantable programmable defibrillator.

FIG. 10 illustrates directly sent waveform paths 68 and 70 traveling, respectively, through the right ventricle 28, to the patch electrode 20, and to the can electrode 14. The shock electrode 38 is not connected.

Figure 11:
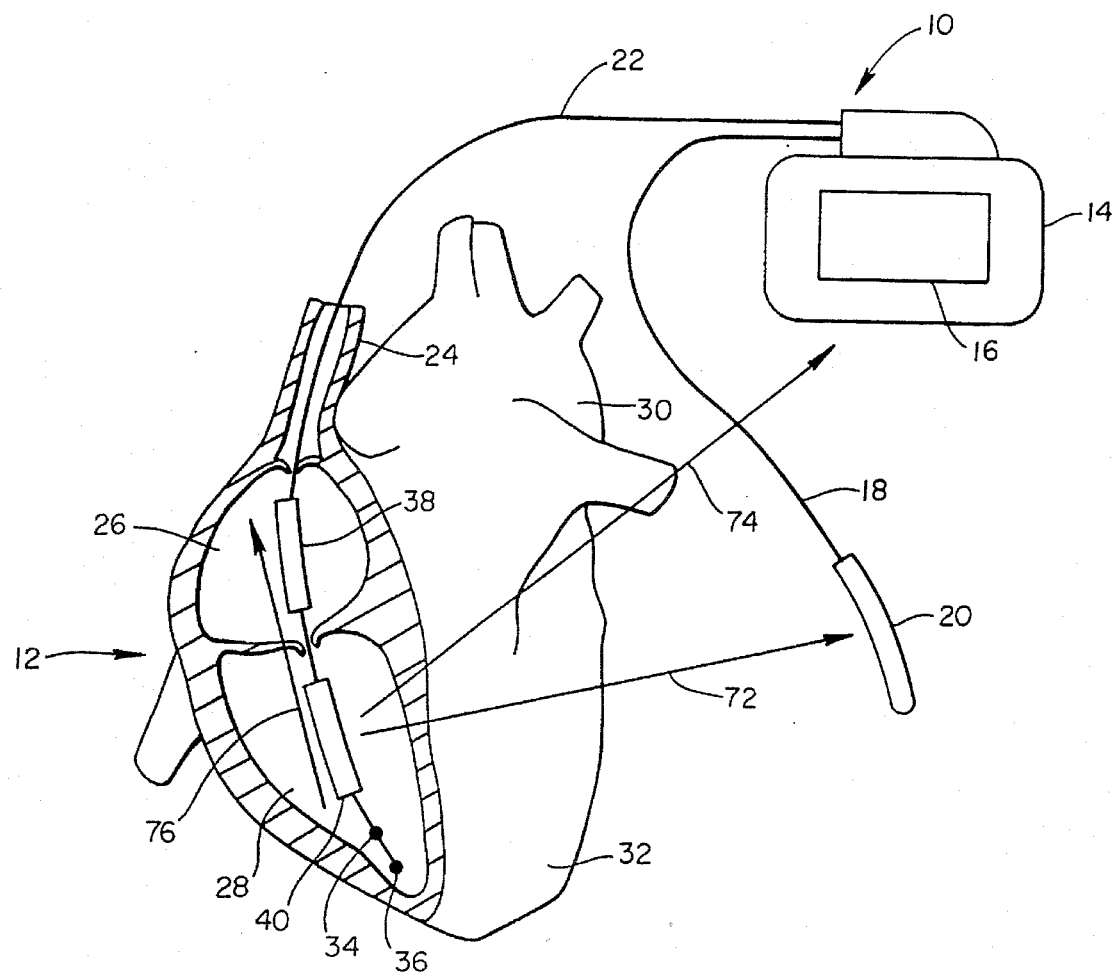
FIG. 11 illustrates another set of waveform paths from the heart to the implantable programmable defibrillator.

FIG. 11 illustrates directly sent waveform paths 72, 74 and 76 traveling, respectively, through the right ventricle 28, to the patch electrode 20, to the can electrode 14, and to the electrode 38 in the superior vena cava 24.

Figure 12:
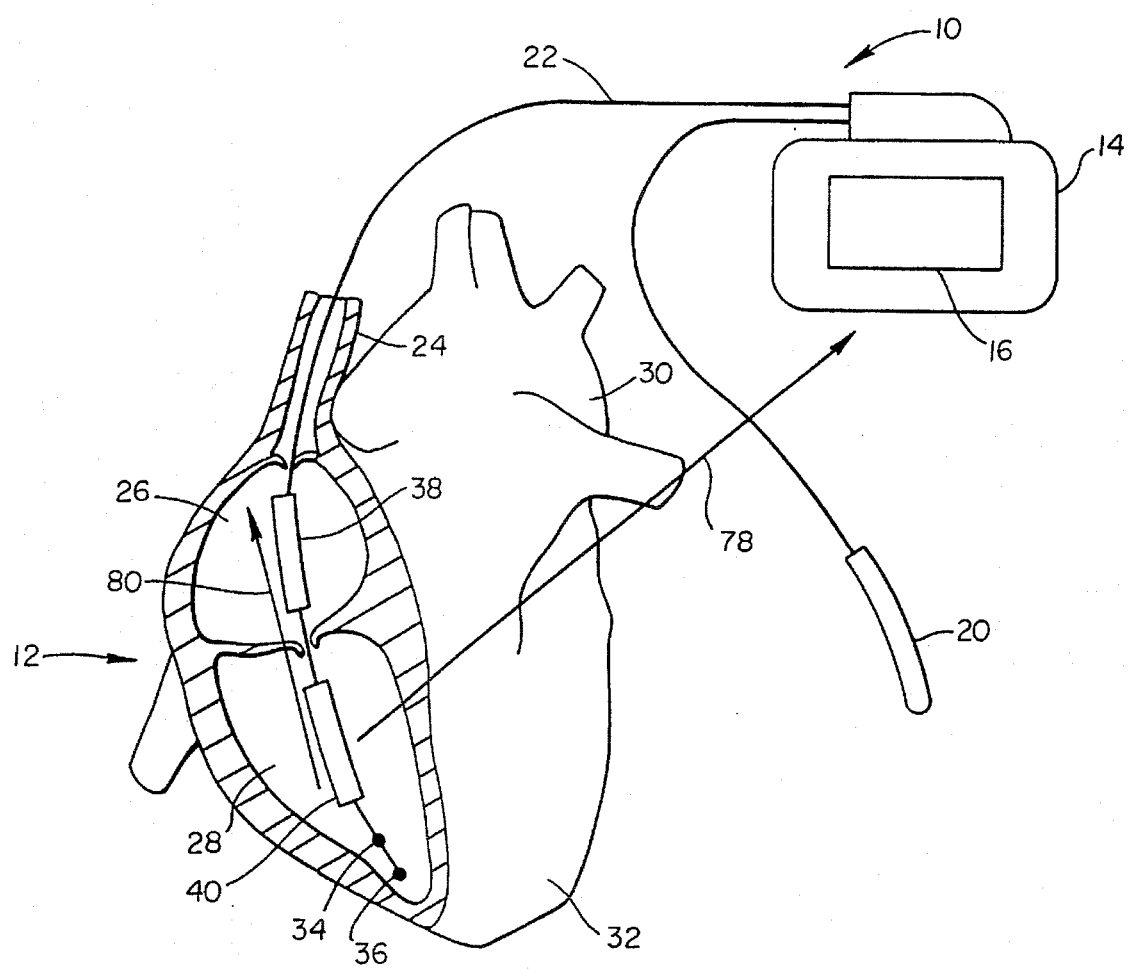
FIG. 12 illustrates another set of waveform paths from the heart to the implantable programmable defibrillator.

FIG. 12 illustrates directly sent waveforms paths 78 and 80 traveling, respectively, through the right ventricle 28, to the can electrode 14 and to the superior vena cava 24. The patch electrode is not connected.

Figure 13:
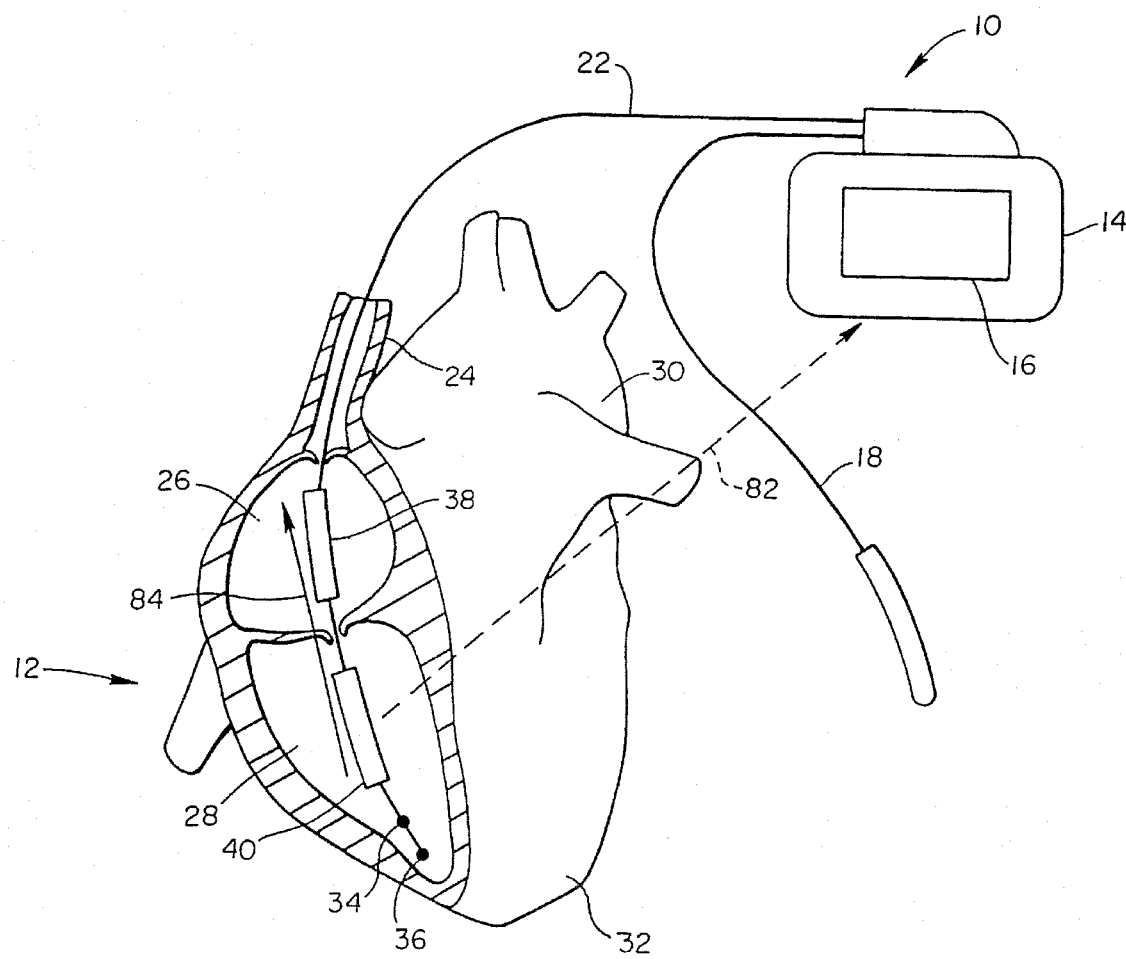
FIG. 13 illustrates another set of waveform paths from the heart to the implantable programmable defibrillator.

FIG. 13 illustrates a delayed shock waveform path 82 traveling through the right ventricle 28, to the can electrode 14, and a directly sent wave path 84 traveling from the right ventricle 28, to the electrode 38 in the superior vena cava 24. The patch electrode 20 is not connected.

Figure 14:
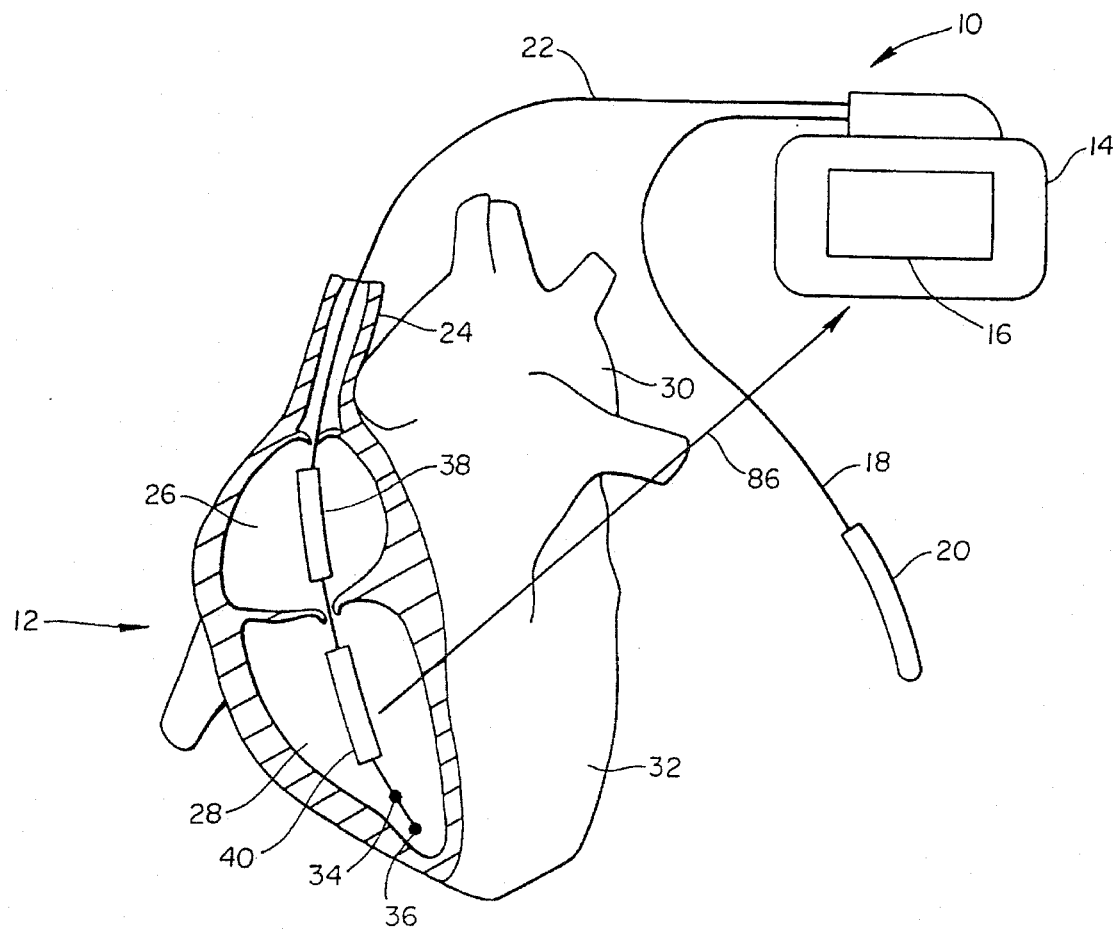
FIG. 14 illustrates another set of waveform paths from the heart to the implantable programmable defibrillator.

FIG. 14 illustrates a directly sent shock waveform path 86 traveling through the right ventricle 28, to the can electrode 14. The shock electrodes 38 and the patch electrode 20 are not connected.

Figure 15:
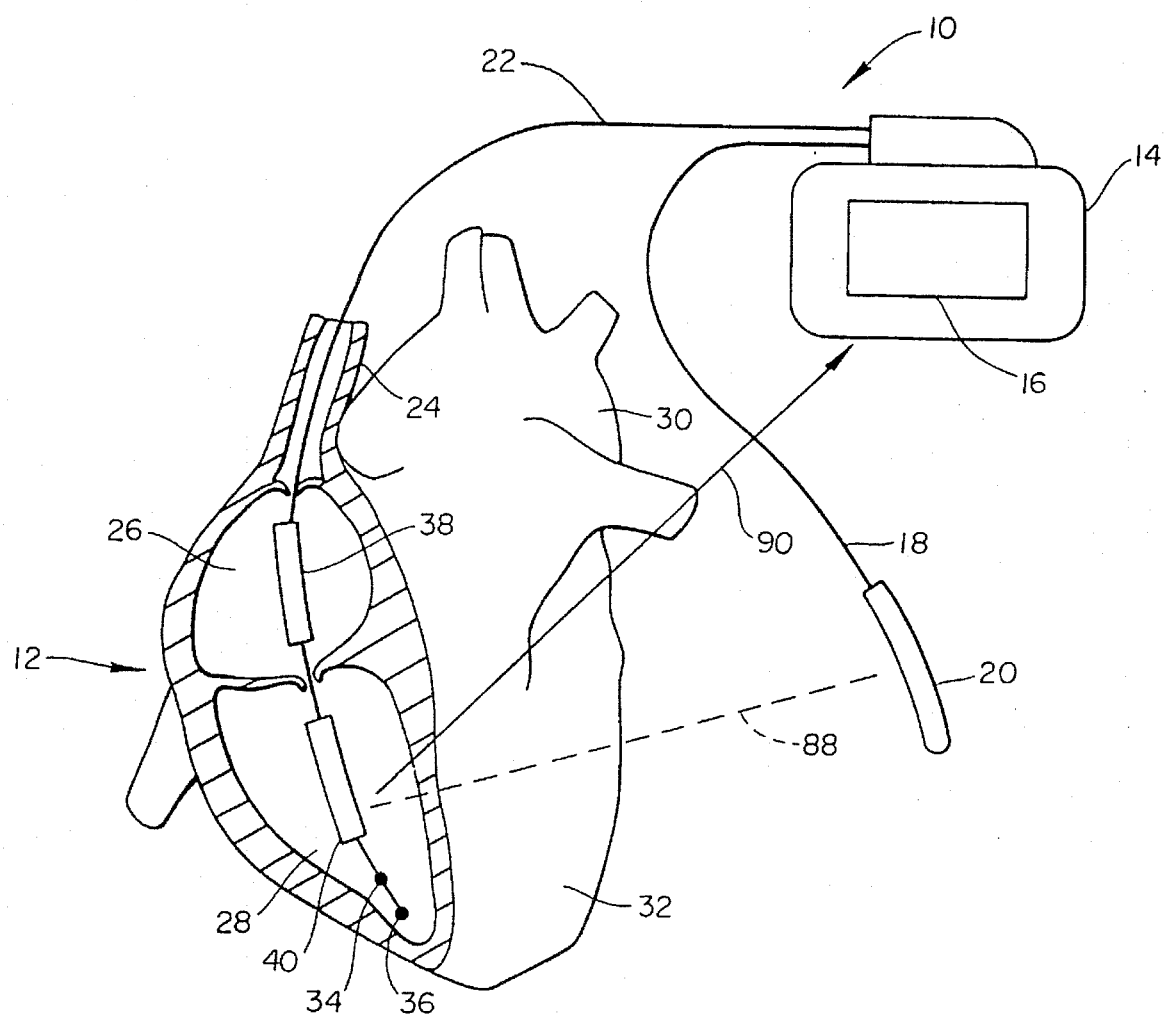
FIG. 15 illustrates another set of waveform paths from the heart to the implantable programmable defibrillator.

FIG. 15 illustrates a delayed shock waveform path 88 traveling through the right ventricle 28, to the patch electrode 20, and a directly sent shock waveform path 90 traveling through the right ventricle, to the can electrode 14. The shock electrode 38 is not connected.

Figure 16:
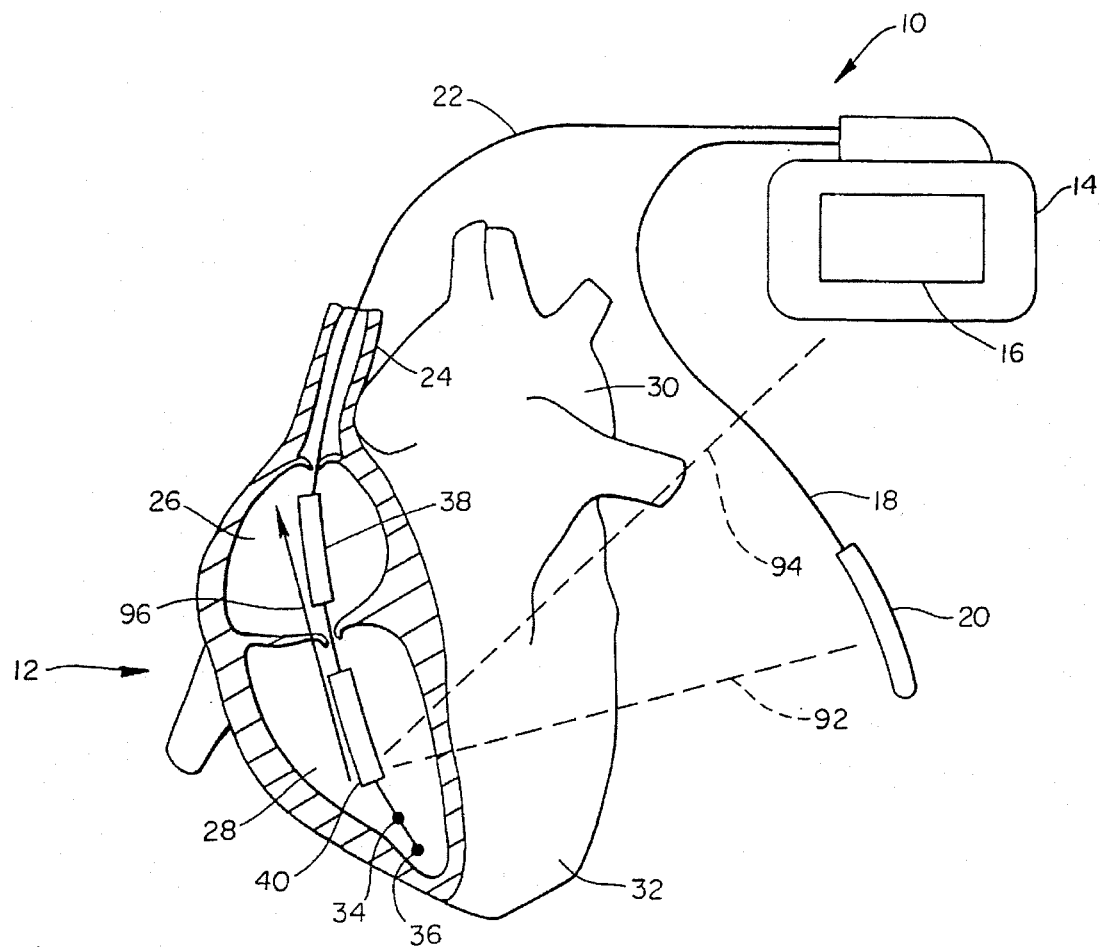
FIG. 16 illustrates another set of waveform paths from the heart to the Implantable programmable defibrillator.

FIG. 16 illustrates delayed shock waveform paths 92 and 94 traveling, respectively, through the right ventricle 28, to the patch electrode 20, and the can electrode 14, and a directly sent shock wave path 96 traveling through the right ventricle 28, to the electrode 38 in the superior vena cava 24.

Figure 17:
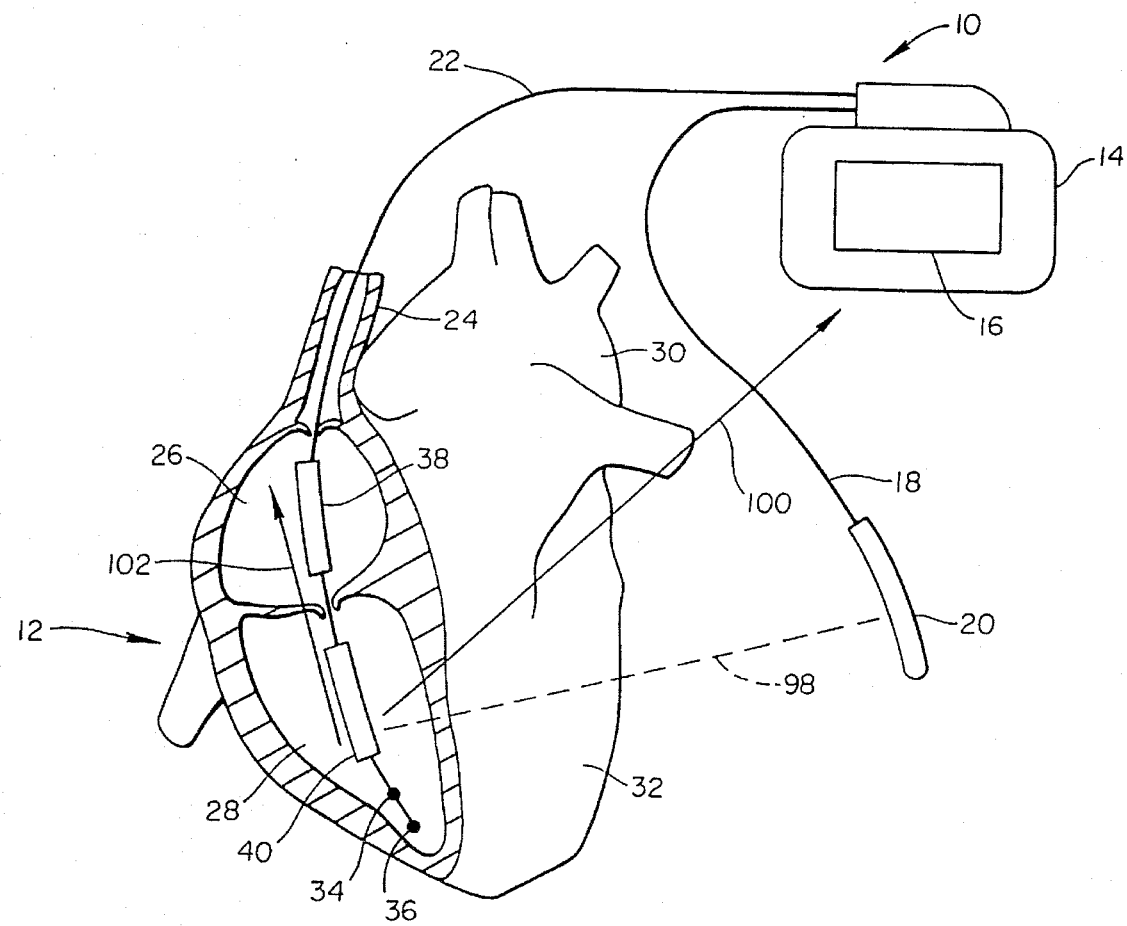
FIG. 17 illustrates another set of waveform paths from the heart to the implantable programmable defibrillator.

FIG. 17 illustrates a delayed shock waveform path 98 traveling through the right ventricle 28, to the patch electrode 20, and directly sent shock waveform paths 100 and 102 traveling, respectively, through the right ventricle 28, to the can electrode 14 and the electrode 38 in the superior vena cava 24.

Figure 18:
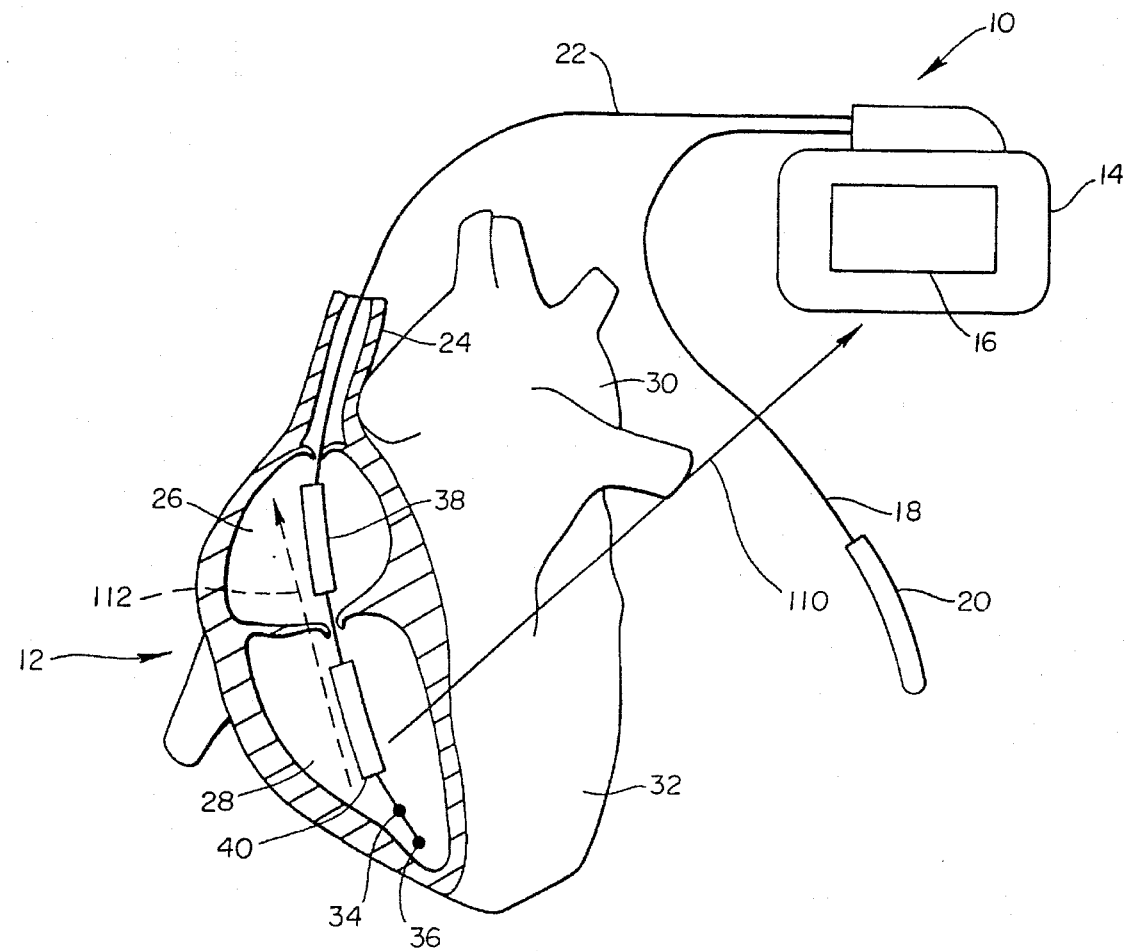
FIG. 18 illustrates another set of waveform paths from the heart to the implantable programmable defibrillator.

FIG. 18 illustrates a directly sent waveform path 110 traveling through the right ventricle 28, to the patch electrode 20, and a delayed shock waveform path 112 traveling through the right ventricle, to the electrode 38 in the superior vena cava 24. The patch electrode 20 is not connected.

TABLE 1

| Atrial area (SVC etc.) | SubQ patch | Can | FIG |
|---|---|---|---|
| delayed | direct (full) | delayed | 6 |
| zero | direct (full) | zero | 7 |
| delayed | direct (full) | direct (full) | 8 |
| zero | direct (full) | delayed | 9 |
| zero | direct (full) | direct (full) | 10 |
| direct (full) | direct (full) | direct (full) | 11 |
| direct (full) | zero | direct (full) | 12 |
| direct (full) | zero | delayed | 13 |
| zero | zero | direct (full) | 14 |
| zero | delayed | direct (full) | 15 |
| direct (full) | delayed | delayed | 16 |
| direct (full) | delayed | direct (full) | 17 |
| delayed | zero | direct (full) | 18 |
| zero | direct (full) | zero | Not shown |
| delayed | direct (full) | zero | Not shown |
| direct (full) | zero | zero | Not shown |
| direct (full) | delayed | zero | Not shown |
| direct (full) | direct (full) | zero | Not shown |
| direct (full) | direct (full) | delayed | Not shown |
| delayed | delayed | direct (full) | Not shown |

Table 1 sets forth the atrial area, the sub Q patch, the can and the corresponding figure. The pulse is either a monophasic pulse or biphasic pulse.

Various modifications can be made to the present invention without departing from the apparent scope hereof.

We claim:

1. An improved implantable defibrillator system adapted to be implanted in a human patient for producing a capacitive-discharge countershock, the implantable defibrillator system being a self-contained device including a capacitor system, a battery system, a switching system and a sensing system all of which are connected to and controlled by a programmable computer system having a memory for storing a plurality of physician programmable charging voltage parameters, one parameter for each countershock in a sequence of countershocks to be delivered to the human patient as part of a multiple-countershock therapy regimen, and computer programming stored in the memory and executing in the computer system that, in response to an initial cardiac arrhythmia in the human patient sensed by the sensing system, selectively charges the capacitor system from the battery system in accordance with a first of the charging voltage parameters stored in the memory for the multiple-countershock therapy regimen and then selectively discharges the capacitor system as a first of the sequence of multiple countershocks delivered through the switching system to a plurality of electrodes adapted to be implanted in the human patient, after which, in response to a continuing cardiac arrhythmia in the human patient sensed by the sensing system, selectively charges the capacitor system from the battery system in accordance with a second of the charging voltage parameters stored in the memory for the multiple-countershock therapy regimen and then selectively discharges the capacitor system as a second of the sequence of multiple countershocks, the improvement comprising:

a data structure located in the memory for defining a plurality of different possible waveforms and a plurality of different possible wavepaths for individual countershocks in the multiple-countershock therapy regimen by storing a plurality of sets of physician programmable waveform parameters in the data structure, a unique set of waveform parameters being associated with each countershock in the sequence of multiple countershocks, the waveform parameters including both wave phase information and wave path information such that each set of waveform parameters defines a selected one of the different possible waveforms and defines a selected one of the different possible wave paths definable in the data structure; and computer programming stored in the memory and executing in the computer system that selectively charges and then discharges the capacitor system in accordance with a first one of the unique sets of waveform parameters stored in the data structure as a first countershock in the sequence of multiple countershocks and, in response to a continuing cardiac arrhythmia in the human patient sensed by the sensing system, selectively charges and discharges the capacitor system in accordance with a subsequent one of the unique sets of waveform parameters stored in the data structure as a subsequent countershock in the sequence of multiple countershocks, such that the first and subsequent countershocks delivered by the implantable defibrillator system as part of the sequence of multiple countershocks can be independently programmed for different waveforms and wave paths.

2. An improved method of operating an implantable defibrillator system adapted to be implanted in a human patient for producing a capacitive-discharge countershock, the implantable defibrillator system being a self-contained device electrically connected to a plurality of electrodes adapted to be implanted in the human patient, the device including a capacitor system, a battery system, a switching system and a sensing system all of which are connected to and controlled by a programmable computer system having a memory and computer programming stored in the memory and executing in the computer system that performs the computer-implemented steps of:

(a) using the sensing system to sense a cardiac arrhythmia in the human patient;

(b) in response to the cardiac arrhythmia, selectively charging the capacitor system from the battery system in accordance with a first of a plurality of physician programmable charging voltage parameters stored in the memory for a first of a sequence of multiple countershocks;

(c) selectively discharging the capacitor system as the first of the sequence of multiple countershocks delivered through the switching system to the plurality of electrodes in accordance with a single set of physician programmable waveform parameters stored in the memory, (d) using the sensing system to sense if the cardiac arrhythmia in the human patient has been converted;

(e) if the cardiac arrhythmia has not been converted, selectively charging the capacitor system from the battery system in accordance with a subsequent one of the plurality of physician programmable charging voltage parameters stored in the memory for a subsequent one of the sequence of multiple countershocks;

(f) selectively discharging the capacitor system as a subsequent one of the sequence of multiple countershocks delivered through the switching system to the plurality of electrodes in accordance with the same single set of physician programmable waveform parameters stored in the memory for the first of the sequence of multiple countershocks; and (g) repeating steps (d)–(f) for other subsequent ones of the multiple countershocks until the cardiac arrhythmia has been converted or the entire sequence of multiple countershocks has been delivered, wherein the improved method comprises implemented steps of:

storing in a data structure defined in the memory a plurality of sets of physician programmable waveform parameters, a unique set of waveform parameters for each countershock in the sequence of multiple countershocks, the waveform parameters including both wave phase information and wave path information such that each set of waveform parameters defines a selected one of a plurality of different possible waveforms and defines a selected one of a plurality of different possible wave paths definable in the data structure; and selectively discharging the capacitor system in step (c) in accordance with a first one of the unique sets of waveform parameters stored in the data structure, and selectively discharging the capacitor system in step (f) in accordance with a subsequent one of the unique sets of waveform parameters stored in the data structure for each subsequent countershock in the sequence of multiple countershocks, such that the first and subsequent countershocks delivered by the implantable defibrillator system as part of the sequence of multiple countershocks can be independently programmed for different waveforms and wave paths.

3. A method of operating an implantable cardioverter defibrillator system adapted to be implanted in a patient for delivering a sequence of capacitive-discharge countershocks to the heart of the patient as part of a multiple-countershock therapy regimen for treating a continuing cardiac arrhythmia in the patient, the implantable defibrillator system having a sensing system, a battery system and a capacitor system, all of which are connected to and controlled by a programmable computer having a memory, the method comprising the steps of:

(a) programming a first set of waveform parameters in the memory in the programmable computer to define a first countershock in the sequence of multiple countershocks, the first countershock having a waveform that is individually selected and programmed by a physician;

(b) programming at least one set additional set of waveform parameters in the memory in the programmable computer to define at least one subsequent countershock in the sequence of multiple countershocks, the subsequent countershock having a waveform that is independent of the waveform of the first countershock and that is individually selected and programmed by the physician;

(c) using the sensing system to sense a cardiac arrhythmia in the patient;

(d) in response to a cardiac arrhythmia, using the battery system to charge the capacitor system to delivery a first countershock to the patient;

(e) discharging the capacitor system in accordance with the first set of waveform parameters stored in the memory programmed in step (a) to deliver the first countershock to the patient;

(f) sensing whether the cardiac arrhythmia in the patient has been converted;

(g) if the cardiac arrhythmia has not been converted, using the battery system to recharge the capacitor system to deliver a subsequent countershock to the patient;

(h) discharging the capacitor system in accordance with a subsequent set of waveform parameters stored in the memory programmed in step (b) to deliver a subsequent countershock to the patient, the subsequent countershock having a waveform that is independent of the waveform of at least one other countershock in the sequence of multiple countershocks and that is individually programmed in step (b); and (i) repeating steps (f)–(h) until the cardiac arrhythmia has been converted or the entire sequence of multiple countershocks has been delivered.

4. The method of claim 3, wherein:

step (a) further includes programming the memory in the programmable computer to define the set of waveform parameters for the first countershock as having a first wave path;

step (b) further includes programming the memory in the programmable computer to define the set of waveform parameters for a subsequent countershock as having a wave path that is independent of the wave path of at least one other countershock in the sequence of multiple countershocks;

step (e) further includes discharging the capacitor system in accordance with the first set of waveform parameters programmed in step (a) to deliver the first countershock having the wave path individually programmed in step (a); and step (h) further includes discharging the capacitor system in accordance with the subsequent sets of waveform parameters programmed in step (b) to deliver a subsequent countershock having a wave path that is independent of the wave path of at least one other countershock in the sequence of multiple countershocks and that is individually programmed in step (b).

5. A self-contained implantable defibrillator system adapted to be implanted in a patient for producing a sequence of multiple capacitive-discharge countershocks to the heart of the patient as part of a multiple-countershock therapy regimen for treating a continuing cardiac arrhythmia in the patient, the system comprising:

a countershock delivery system for delivering the sequence of multiple countershocks to the patient, the countershock delivery system including a capacitor system and a battery system coupled with the capacitor system to charge the capacitor system;

a sensing system to detect a cardiac arrhythmia in the patient;

a programmable computer means, coupled with the countershock delivery system and with the sensing system, the programmable computer means including:

means for storing data defining the waveform of each countershock independently, such that each delivered countershock can be programmed to have a waveform different than and independent of the waveform of any other countershock in the sequence of multiple countershocks; and means for directing delivery of each countershock in the sequence of multiple countershocks through the countershock delivery system in accordance with detection of a cardiac arrhythmia by the sensing system; and means for delaying delivery of each subsequent countershock after the first countershock in the sequence of multiple countershocks until the sensing system detects if the cardiac arrhythmia in the patient has been converted in response to a previous countershock and the battery system has charged the capacitor system for delivery of the subsequent countershock.

6. The defibrillator system of claim 5, wherein the programmable computer means further comprises means for storing data defining the wave path of each countershock independently, such that each delivered countershock can be programmed to have a wave path different than and independent of the wave path of any other countershock in the sequence of multiple countershocks.

* * * * *